United States Patent [19]

Strike

[11] 4,091,015

[45] May 23, 1978

[54] 15-SUBSTITUTED PROSTANOIC ACIDS

[75] Inventor: Donald P. Strike, St. Davids, Pa.

[73] Assignee: American Home Products Corporation, New York, N.Y.

[21] Appl. No.: 470,772

[22] Filed: May 17, 1974

Related U.S. Application Data

[63] Continuation-in-part of Ser. No. 301,571, Oct. 27, 1972, abandoned, and Ser. No. 462,006, Apr. 18, 1974, abandoned, which is a continuation-in-part of Ser. No. 383,007, Jul. 26, 1973, Pat. No. 3,922,302.

[51] Int. Cl.$^2$ .......................................... C07C 177/00
[52] U.S. Cl. ..................... 260/520 B; 260/514 D; 424/305; 424/308; 424/317; 560/53; 560/121
[58] Field of Search ............... 260/468, 514, 473, 520

[56] References Cited

U.S. PATENT DOCUMENTS 3,804,889  4/1974  Bundy ................... 260/514

FOREIGN PATENT DOCUMENTS 2,353,788  5/1974  Germany ............... 260/468
2,364,706  7/1974  Germany ............... 260/468

*Primary Examiner*—Robert Gerstl
*Attorney, Agent, or Firm*—Robert Wiser

[57] ABSTRACT

9-Oxo-15-Substituted prostanoic acids, and intermediates for their preparation are disclosed. The final products have bronchodilatory activity.

2 Claims, 2 Drawing Figures

FIGURE I

15-SUBSTITUTED PROSTANOIC ACIDS

This is a continuation-in-part of application Ser. No. 301,571, filed Oct. 27, 1972, now abandoned; and of application Ser. No. 462,006, filed Apr. 18, 1974 now abandoned, which is a continuation-in-part of application Ser. No. 383,007, filed July 26, 1973 now U.S. Pat. No. 3,922,302.

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to process a variety of biological properties such as bronchodilation, the ability to reduce gastric secretion, to modify muscle tone, as well as the ability to raise or lower blood pressure.

Various derivatives of prostaglandins have also been synthesized and reported. 9,15-Dihydroxy prost-13-enoic acid and methods of synthesis thereof are disclosed in U.S. Pat. Nos. 3,432,541 and 3,455,922. 9-Oxo-15-hydroxy-15-methyl-prostanoic acid, 15-oxo-9-hydroxy-prostanoic acid, and 9,15-dioxo-prostanoic acid are disclosed in U.S. Pat. No. 3,671,570.

The present invention concerns new unsaturated 15-polycarbon(lower)alkyl, vinyl and benzyl 9-oxo-15-hydroxy-prostanoic acids and new intermediates thereto.

SUMMARY OF THE INVENTION

The invention sought to be patented in its composition aspect resides in the concept of a chemical compound which is a prostanoic acid of the structure:

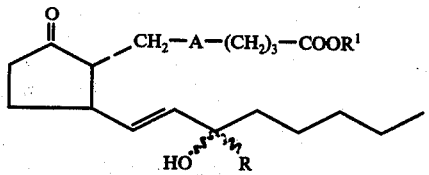

wherein R is ethyl, n-propyl, vinyl, or benzyl, and A is cis—CH=CH—; or R is ethyl, n-propyl or vinyl, and A is —$CH_2$—$CH_2$—; and $R^1$ is hydrogen, alkyl of from 1 to about 6 carbon atoms, alkali metal, or a pharmacologically acceptable cation derived from ammonia or a basic amine.

The tangible embodiments of the first composition aspect of the invention possess the inherent general physical properties of being clear to yellow oils, or crystalline solids, and when $R^1$ is hydrogen are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral date supporting the molecular structures herein set forth. The aforementioned physical characteristics, taken together with the nature of the starting materials and the mode of snythesis confirm the structure of the compositions sought to be patented.

The tangible embodiments of the composition aspect of the invention possess the inherent applied use characteristic of exerting bronchodilating effects upon administration to warm-blooded animals as evidenced by pharmacological evaluation accordind to standard test procedures.

The invention sought to be patented in its first process aspect resides in the concept of a method of relieving bronchial spasm and facilitating breathing in warm-blooded animals which comprises administering to a warm-blooded animal in need thereof an amount sufficient to relieve bronchial spasm and facilitate breathing in said warm-blooded animal of a prostanoic acid of the formula:

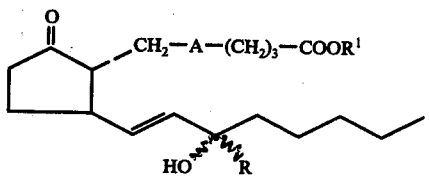

wherein R is ethyl, n-propyl, vinyl, or benzyl, and A is cis—CH=CH—; or R is ethyl, n-propyl, or vinyl, and A is —$CH_2$—$CH_2$—; and $R^1$ is hydrogen, alkyl of from 1 to about 6 carbon atoms, alkali metal, or a pharmacologically acceptable cation derived from ammonia or a basic amine.

The invention sought to be patented in its second process aspect resides in the concept of a process for the preparation of compounds of the formula:

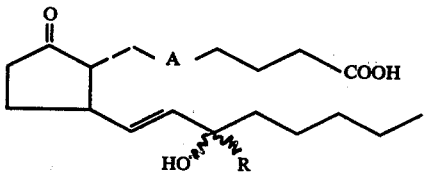

I wherein R is ethyl, n-propyl, vinyl, or benzyl, and A is cis—CH=CH—; or R is ethyl, n-propyl, or vinyl, and A is —$CH_2$—$CH$—$_2$; which comprises treating a compound of the formula:

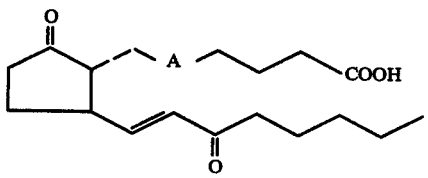

wherein A is as described hereinabove; with a grignard reagent of the formula:

RMgX wherein X is halo and R is ethyl, n-propyl, vinyl, or benzyl; with the proviso that when A is —$CH_2$—$CH_2$—; R is ethyl, n-propyl, or vinyl, at a temperature of from about −78° C to about 0° C. The final products produced by the process aspect of the invention possess the inherent applied use characteristics of exerting bronchodilating effects upon administration to warm-blooded animals.

DESCRIPTION OF THE PREFERRED EMBODIMENTS

Figure 1:
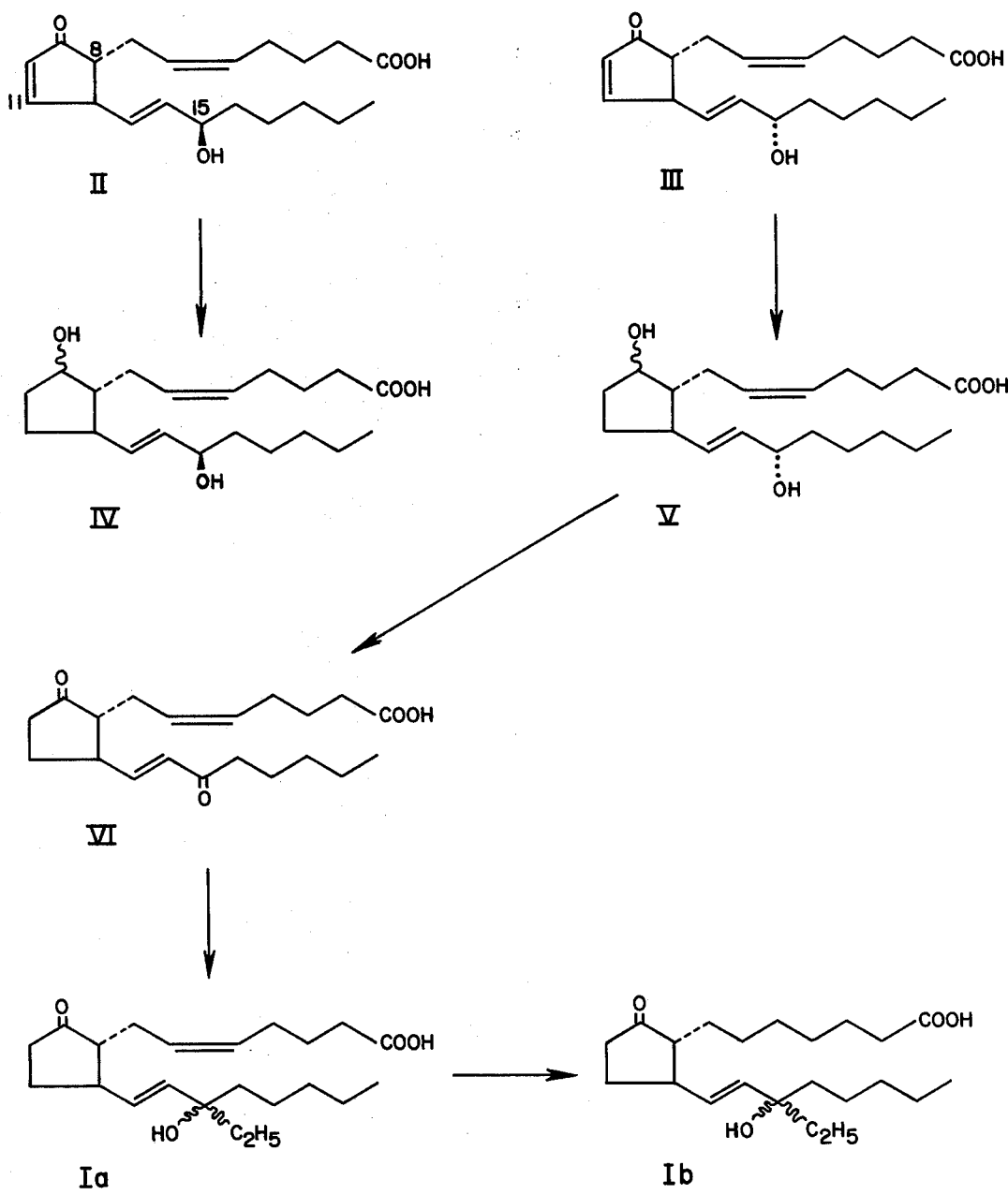

In describing the synthesis of the compositions of the invention reference will be made to FIGS. 1, and 2, wherein the formulae representing the various embodiments of the invention have been assigned Roman numerals for purposes of identification. FIG. 1 illustrates the synthesis of specific embodiments of Formula I namely; 7-(2β-[(3RS)-3-hydroxy-3-ethyl-trans-1-octenyl]-5-oxo-1α-cyclopentyl)-cis-5-heptenoic acid (Ia) and 2β-[(3RS)-3-ethyl-3-hydroxy-trans-1-octenyl]-5-oxo-1α-cyclopentane heptanoic acid (Ib).

Figure 2:
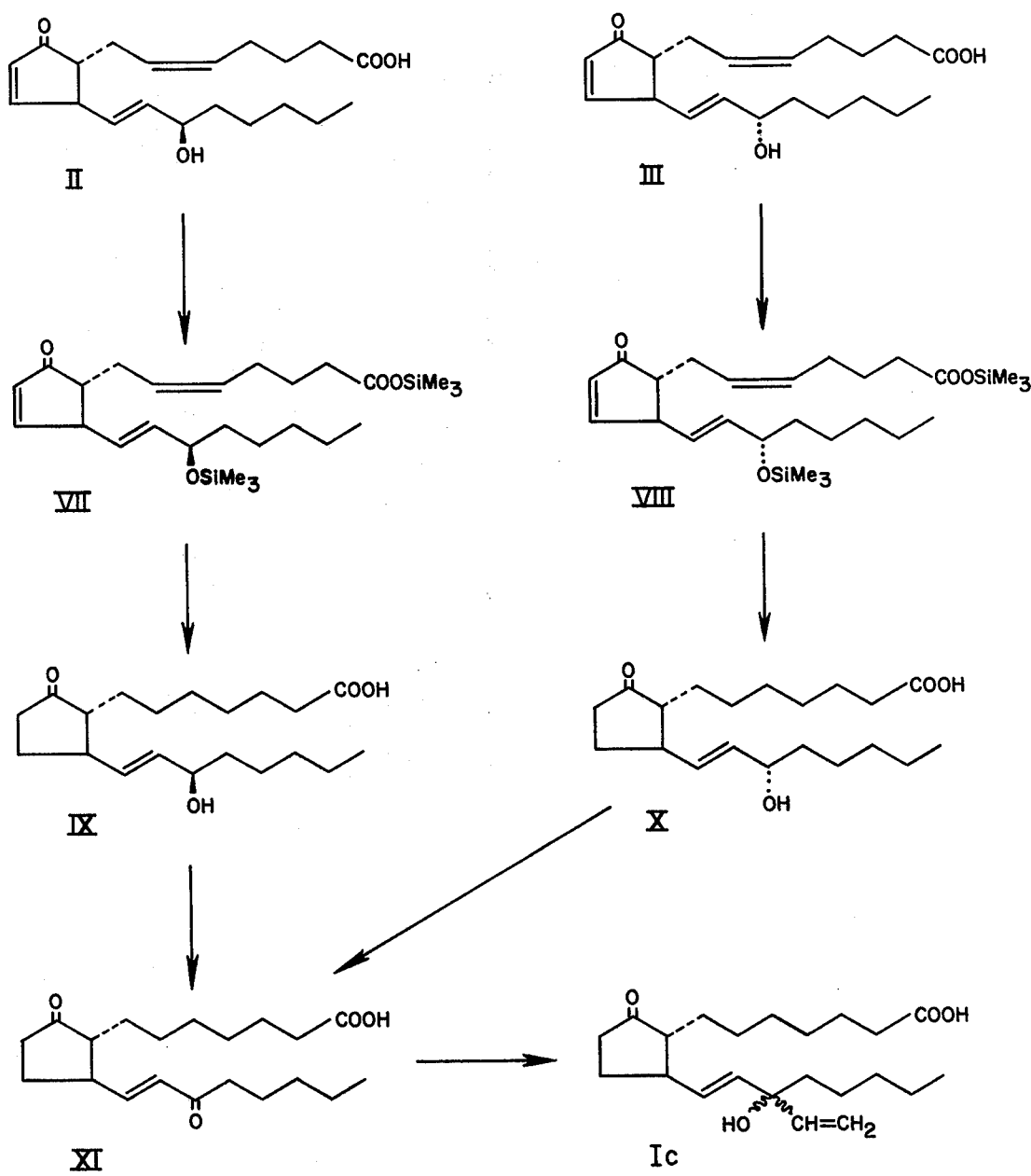

FIG. 2 illustrates the synthesis of another embodiment of Formula I namely 2β-[(3RS)-3-vinyl-3-hydroxy-trans-1-octenyl]-5-oxo-1α-cyclopentane heptanoic acid (Ic).

The starting materials in the synthesis of the compositions of the invention, namely 15-epi PGA$_2$ (II), and PGA$_2$ (III) are well-known in the art. For example, 15-epi PGA$_2$ may be obtained from the coral *Plexaura homomalla* by a procedure as described by A. Weinheimer and R. Spraggins in Tetrahedron Letters, 59, 5185 (1969), and PGA$_2$ may, if desired, be prepared from 15-epi PGA$_2$ by an epimerization procedure as described by Bundy et al. in Annals of the New York Academy of Sciences, 180, 76, (April 30, 1971).

Sodium borohydride reduction of either II or III yields 7-[2β-(3-hydroxy-trans-1-ocetenyl)-5ξ-hydroxy-1α-cyclopentyl]-cis-5-heptenoic acid (IV and V) where the orientation of the hydroxy group in the 3 position of the octenyl side chain corresponds to that of the starting material. Oxidation of either IV or V by standard techniques, conveniently by treatment with Jones reagent gives 7-[2β-3-oxo-trans-1-octenyl)-5-oxo-1α-cyclopentyl]-cis-5-heptenoic acid (VI). Treatment of VI with ethyl Grignard reagent at reduced temperature, conveniently at about 0° or less, gives 7-(2β-[(3RS)-3-ethyl-3-hydroxy-trans-1-octenyl]-5-oxo-1α-cyclopentyl)-cis-5-heptenoic acid (Ia). If desired, Ia may be isolated by standard techniques. Chromatography on a silica gel column is a convenient method. Selective reduction of the double bond in the heptenoic acid side chain, conveniently by treatment with hydrogen in the presence of tris(triphenylphosphine)rhodium (I) chlorine, gives 2β-[(3RS)-3-ethyl-3-hydroxy-trans-1-octenyl]-5-oxo-1α-cyclopentane-heptanoic acid (Ib). If desired, Ib may be isolated by standard techniques. Chromatography on a silica gel column is a convenient method.

It will be obvious to substitute other Grignard reagents, such as n-propyl; benzyl; or vinyl Grignard reagent, for the ethyl Grignard reagent illustrated so as to prepare the analogs of Ia contemplated within the scope of Formula I. The conversion of the n-propyl derivative to an analog of Ib by the method indicated above will similarly be obvious.

An alternative synthesis is suitable for the preparation of Ib and compounds analogous thereto, and is particularly suitable when a vinyl substituent therein is desired. The carboxylic and 15-hydroxyl groups of II and III are protected, conveniently by conversion to the trimethylsilyl derivatives VII and VIII respectively. Treatment of VII or VIII with hydrogen in the presence of a catalyst, conveniently tris(triphenylphosphine)rhodium (I) chloride, followed by cleavage of the silyl protecting groups, conveniently by contacting with aqueous acid, gives 2β-[(3R)-3-hydroxy-trans-1-octenyl]-5-oxo-1α-cyclopentaneheptanoic acid (IX) and 2β-[(3S)-3-hydroxy-trans-1-octenyl]-5-oxo-1α-cyclopentaneheptanoic acid (X) respectively. IX or X may, if desired, be isolated by standard techniques. Chromatography on a silica gel column is a convenient method. Oxidation of IX or X, conveniently with Jones reagent, gives 2β-(3-oxo-trans-1-octenyl)-5-oxo-1α-cyclopentaneheptanoic acid (XI). If XI is treated with vinyl Grignard reagent at reduced temperature, conveniently at about −78°, 2β-[(3RS)-3-hydroxy-3-vinyl-trans-1-octenyl]-5-oxo-1α-cyclopentane heptanoic acid (Ic) is produced. If desired, Ic may be isolated by standard procedures. Chromatography on a silica gel column in a convenient method. The use of ethyl, or n-propyl Grignard reagents in place of vinyl Grignard reagent to produce Ib or its n-propyl analog will be obvious to one skilled in the art.

It will be apparent to those skilled in the art of chemistry that the carbon atoms on the octane side chain to which hydroxyl substituents are attached are assymetric carbon atoms, and as a consequence these positions can be either of two epimeric configurations. The symbol where used in this specification is to indicate that both possible configurations at each particular position is intended and is included within the scope of the invention.

The esters of formula I (R$^1$ is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of the invention can be prepared by mixing stoichiometrically equivalent amounts of the free acids of formula I, preferably in aqueous solution, with solutions of alkali metal bases, such as sodium, potassium, and lithium hyroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "alkyl of from about 1 to about 6 carbon atoms" when used herein and in the appended claims includes straight and branched chain hydrocarbon radicals, illustrative members of which are methyl, ethyl, n-propyl, i-propyl, n-butyl, t-butyl, n-pentyl, n-hexyl, 3-methylpentyl, 2,3-dimethylbutyl, and the like. "Alkali metal" includes, for example, sodium, potassium, lithium, and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

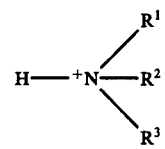

wherein R$^1$, R$^2$, and R$^3$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or mono-carbocyclicarylhydroxyalkyl of from about 7 to about 15 carbon atoms, or, when taken together with the nitrogen atom to which they are attached, any two of $R^1$, $R^2$, and $R^3$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-di- and triethanolammonium, ethylidiethanolammonium, n-butylmonoethanolammonium, tris(hydroxymethyl)-methylammonium, phenylmonoethanolammonium, and the like.

In practicing the method of the invention, the instant compositions can be administered in a variety of dosage forms, the oral route being used primarily for maintenance therapy while injectables tend to be more useful in acute emergency situations. Inhalation (aerosols and solution for nebulizers) seems to be somewhat faster acting than other oral forms but slower than injectables and this method combines the advantages of maintenance and moderately-acute stage therapy in one dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example a hand nebulizer or a pressurized aerosol dispenser the dose is from about 5 micrograms to about 100 micrograms, and preferably from about 10 to about 50 micrograms, approximately every four hours, or as needed. By theoral ingestion route, the effective dose is from about 1 to about 20 mg., preferably from about 5 to about 15 mg. up to a total of about 40 mg. per day. By the intravenous route, the ordinarily effective dose is from about 50 micrograms to about 300 micrograms, preferably about 200 micrograms per day.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart bronchodilating activity thereto. This will range upward from about 0.0001% by weight of active ingredient in said composition.

For administration by the oral inhalation route with conventional nebulizers or by oxygen aerosolization it is convenient to provide the instant active ingredient in dilute aqueous solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a so-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. Nos. 2,868,691 and 3,095,355, for example.

The following examples further illustrate the best mode contemplated by the inventor of making the compositions of the invention.

EXAMPLE 1

7-[2β-(3-Oxo-Trans-1-Octenyl)-5-Oxo-1α-Cyclopentyl]-Cis-5-Heptenoic Acid

A solution of 4.0 g. of 15-epi-$PGA_2$ in 110 ml. of 10:1 mixture of methanol-water is treated at 0° C. with 2.2 g. of sodium borohydride and stirred at 25° C. for 7 hours. The mixture is acidified at 0° C. with acetic acid and evaporated under vacuum to almost dryness. The resulting residue is diluted with water and extracted with ether. After washing with water and drying over magnesium sulfate, the extract is evaporated. The resulting residue is dissolved in 350 ml. of acetone and treated at 0° C. with 30 ml. of 1.4M Jones reagent for ¾ hour. The mixture is neutralized with sodium bicarbonate solution, acidified with acetic acid and extracted with ether. After washing with water and drying over magnesium sulfate, the extract is evaporated and the residue chromatographed on silica gel. Elution with 30% ethyl acetate in hexane affords 3.3 g. of the title product as an oil, $\lambda_{max}^{film}$ 3.45, 5.75, 5,85, 6.0, 6.15, 6.85, 7.1, 7.2, 8.7, 10.2 μ. UV: $\lambda_{max}^{EtOH}$ 228 mμ (ε 11,860). NMR: δ 0.90 (t, 3, methyl); 5.40 (m, 2, 5 and 6 H); 6.18 (J=16, 14-H); 6.86 (dd, J=16 and 7.5, 13-H); 10.72 (s, 1, OH) ppm.

Analysis for: $C_{20}H_{30}O_4$; Calculated: C, 71.82; H, 9.04; Found: C, 72.01; H, 9.00.

EXAMPLE 2

7-(2β-[(3RS)-3-Ethyl-Hydroxy-Trans-1-Octenyl]-5-Oxo-1α-Cyclopentyl)-Cis-5-Heptenoic Acid A solution of 0.45 g. of 7-[2β-(3-oxo-trans-1-octenyl)-5-oxo-1α-cyclopentyl]-cis-5-heptenoic acid in 30 ml. of THF is treated at 0° C. with 1.7 ml. of 3M ethyl magnesium bromide and stirred at 0° C. for 20 minutes. The mixture is added to aqueous ammonium chloride solution acidified with acetic acid and extracted with ether. After washing with water and drying over magnesium sulfate, the extract is evaporated and the residue chromatographed on silica gel. Elution with 20% ethyl acetate in hexanes affords 0.13 g. of the title product as an oil, $\lambda_{max}^{film}$ 2.9, 3.4, 5.75, 6.8, 10.2 μ. NMR: δ 0.89 (t, 20-$CH_3$), 0.98 (t, $CH_3$ at 15-substituted ethyl), 5.2 to 5.92 (m, 4, olefin H), 6.32 (s, 3, OH) ppm. Mass spectrum: $M^+$—$H_2O$ at m/e 346 (theory 346).

EXAMPLE 3

7-(2β-[(3RS)-3-Hydroxy-3-Propyl-Trans-1-Octenyl]-5-Oxo-1α-Cyclopentyl)-Cis-5-Heptenoic Acid A solution of 2.0 g. of 7-(2β-(3-oxo-trans-1-octenyl)-5-oxo-1α-cyclopentyl]-cis-5-heptenoic acid in 80 ml. of THF is treated at −78° C. with 9.5 ml. of 2.2M n-propyl magnesium chloride and stirred at −78° C. for 15 minutes. The mixture is added to aqueous ammonium chloride solution, acidified with acetic acid and extracted with ether. After washing with water and drying over magnesium sulfate, the extract is evaporated and the residue chromatographed on silica gel. Elution with 20% ethyl acetate in hexanes affords 0.76 g. of the title product as an oil, $\lambda_{max}^{film}$ 2.9, 3.4, 5.75, 6.8, 7.05, 7.2, 8.6, 9.2 μ. NMR: δ 0.92 (m, 6, terminal methyls); 5.51 (m, 2, 5 and 6-H); 5.63 (m, 2, 13 and 14-H); 6.97 (s, 2, OH) ppm. Mass spectrum: $M^+$-$H_2O$ at m/e 360 (theory 360).

EXAMPLE 4

7-(2β-[(3RS)-3-Benzyl-3-Hydroxy-Trans-1-Octenyl]-5-Oxo-1α-Cyclopentyl)-Cis-5-Heptenoic Acid A solution of 0.5 g. of 7-[2β-(3-oxo-trans-1-octenyl)-5-oxo-1α-cyclopentyl]-cis-5-heptenoic acid in 50 ml. of THF is treated at −78° C. with 4.3 ml. of 1.1M benzyl magnesium chloride and stirred at −78° C. for 40 minutes. The mixture is added to aqueous ammonium chloride solution, acidified with acetic acid and extracted with ether. After washing with water and drying over magnesium sulfate, the extract is evaporated and the residue chromatographed on silica gel. Elution with 16% ethyl acetate in hexanes affords 0.3 g. of the title product as an oil, $\lambda_{max}^{film}$ 3.0, 3.45, 5.8, 6.28, 6.70, 6.90, 7.16, 8.7, 10.3, 13.3, 14.3 μ. NMR: δ 0.9 (t, 3, methyl), 2.88 (s, 2, benzylic H), 5.42 (m, 2, 5, and 6-H), 5.55 (m, 2, 13 and 14-H), 6.52 (m, 2, OH), 7.25 (s, 5, aromatic H) ppm. Mass spectrum: $M^+$-$H_2O$ at m/e 408 (theory 408).

EXAMPLE 5

7-(2β-[3RS)-3-Hydroxy-3-Vinyl-Trans-1-Octenyl]-5-Oxo-1α-Cyclopentyl)-Cis-5-Heptenoic Acid A solution of 0.5 g. of 7-[2β-(3-oxo-trans-1-octenyl)-5-oxo-1α-cyclopentyl]-cis-5-heptenoic acid in 50 ml. of THF is treated at −78° C. with 1.9 ml. of 2.8M vinyl magnesium chloride and stirred at −78° C. for 15 minutes. The mixture is added to aqueous ammonium chloride solution, acidified with acetic acid and extracted with ether. After washing with water and drying over magnesium sulfate, the extract is evaporated and the residue chromatographed on silica gel. Elution with 20% ethyl acetate in hexanes affords 0.28 g. of the title product as an oil, $\lambda_{max}^{film}$ 1.9, 3.4, 5.75, 6.8, 7.05, 8.65, 10.25, 10.85 μ. NMR: δ 0.9 (t, 3, methyl); 5.02–6.22 (m, 7, olefinic H); 6.49 (s, 2, OH) ppm. Mass spectrum: $M^+$ at m/e 362 (theory 362).

EXAMPLE 6

2β-[(3RS)-3-Ethyl-3-Hydroxy-Trans-1-Octenyl]-5-Oxo-1α-Cyclopentane Heptanoic Acid A solution of 0.45 g. of 7-(2β-[(3RS)-3-ethyl-3-hydroxy-trans-1-octenyl]-5-oxo-1α-cyclopentyl)-cis-5-heptenoic acid in 30 ml. of 1:1 mixture of benzene-ethanol is mixed with 150 mg. of tris(triphenylphosphine)rhodium chloride. The mixture is hydrogenated at 25° C. and atmospheric pressure until one equivalent of $H_2$ was absorbed. The mixture is evaporated and the residue chromatographed on silica gel. Elution with 20% ethyl acetate affords 165 mg. of the title product as an oil, $\lambda_{max}^{film}$ 3.0, 3.45, 5.75 (shoulder), 5.85, 6.85, 10.3 μ. NMR: δ 0.92 (m, 6, methyls); 5.23 (s, 2, OH); 5.23 (m, 2, olefinic H) ppm. Mass spectrum: $MH^+$ at m/e 367 (theory 367).

EXAMPLE 7

2β-[(3R)-3-Hydroxy-Trans-1-Octenyl]-5-Oxo-1α-Cyclopentane Heptanoic Acid

A solution of 10.5 g. of 15-epi-$PGA_2$ in 65 ml. of tetrahydrofuran is treated with 15 ml. of hexamethyldisilazane and 0.9 ml. of trimethyl chlorosilane and stirred under nitrogen at 25° C. for 2 hours. The solvent is evaporated under vacuum, benzene added to the residue and again evaporated under vacuum.

A solution of the above crude di-TMS derivative and 3.0 g. of tris(triphenylphosphine)rhodium (I) chloride in 550 ml. of 1:1 benzene-absolute ethanol is hydrogenated at 25° C. and atmospheric pressure until 2 equivalents of hydrogen are absorbed. The reaction solution is then treated with 50 ml. of 0.5N hydrochloric acid and stirred at 25° C. for 0.5 hours. After concentrating the solution under vacuum, the residue is treated with benzene, evaporated under vacuum and chromatographed on silica. Elution with 32% ethyl acetate in hexane affords 6.5 g. of the title product, $\lambda_{max}^{film}$ 3.0 (shoulder), 3.45, 5.75, 6.8, 7.1, 8.55, 10.3 μ. NMR: δ 7.18 (s, 2, OH); 5.62 (m, 2, 13, 14-H); 4.15 (m, 1, 15-H) ppm. Mass spectrum: $M^+H$ at m/e 339 (theory 339).

EXAMPLE 8

2β-(3-Oxo-Trans-1-Octenyl)-5-Oxo-1α-Cyclopentane Heptanoic Acid

An ice-cooled solution of 3.1 g. of 2β-[(3RS)-3-hydroxy-trans-1-octenyl]-5-oxo-1α-cyclopentane heptanoic acid in 250 ml. of acetone is treated with 20 ml. of 1.4M Jones reagent and stirred at 0° for 40 minutes. The reaction mixture is then treated with 10 ml. of methanol, neutralized with dilute sodium bicarbonate and acidified with acetic acid. After filtering and concentrating the solution under vacuum, the residue is diluted with water and extracted with ether. The extract is washed with water, dried and evaporated. Silica chromatography of the resulting residue with 20% ethyl acetate in hexane gives 2.55 g. of the title product, $\lambda_{max}^{film}$ 3.45, 5.75, 5.85, 5.95, 6.10, 7.1, 8.65, 10.2 μ. NMR: δ 10.9 (s, 1, OH); 6.88 (dd, J=7.5 and 16, 13-H); 6.22 (d, J=16, 14-H) ppm. Mass spectrum: $M^+$ at m/e 335 (theory 336).

EXAMPLE 9

2β-[(3RS)-3-Hydroxy-3-Vinyl-Trans-1-Octenyl]-5-Oxo-1α-Cyclopentane Heptanoic Acid A solution of 0.4 g. of 2β-(3-oxo-trans-1-octenyl)-5-oxo-1α-cyclopentane heptanoic acid in 40 ml. of THF is treated at −78° C. with 1.6 ml. of 2.8M vinyl magnesium chloride and stirred for 15 minutes. The mixture is added to aqueous ammonium chloride solution, acidified with acetic acid and extracted with ether. After washing with water, and extract is evaporated and the residue chromatographed on silica gel. Elution with 20% ethyl acetate in hexanes affords 0.27 g. of the title product as an oil, $\lambda_{max}^{film}$ 3.0 (shoulder), 3.4, 5.8, 6.8, 7.1, 8.65, 10.05, 10.85 μ. NMR: δ 0.89 (t, 3, methyl); 5.0–6.30 (m, 5, olefinic H); 6.63 (m, 2, OH) ppm. Mass spectrum: $M^+$ at m/e 364 (theory 364).

EXAMPLE 10

2β-[(3RS)-3-Hydroxy-3-Propyl-Trans-1-Octenyl]-5-Oxo-1α-Cyclopentane Heptanoic Acid A solution of 0.66 g. of 7-(2β-[(3RS)-3-hydroxy-3-propyl-trans-1-octenyl]-5-oxo-1α-cyclopentyl)-cis-5-heptenoic acid 30 ml. of 1:1 mixture of benzene-ethanol is mixed with 150 mg. of tris(triphenylphosphine)rhodium chloride. The mixture is hydrogenated at 25° C. and atmospheric pressure until one equivalent $H_2$ is absorbed. The mixture is evaporated and the residue chromatographed on silica gel. Elution with 25% ethyl acetate in hexanes affords 0.59 g. of the title product as an oil, $\lambda_{max}^{film}$ 2.95, 3.5, 5.8, 6.85, 7.1, 7.25, 8.65, 10.3 μ. NMR: δ 0.91 (m, 6, methyls); 5.59 (m, 2, olefinic H); 6.42 (s, 2, OH) ppm. Mass spectrum: $M^+$-$H_2O$ at m/e 362 (theory 362).

EXAMPLE 11

A. Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine (ACH) was administered at doses of 10 to 40 mcg/kg. depending on each animal's sensitivity to this compound, and control responses to acetylcholine were thus established. Bronchoconstrictor agents raise the resistance of the lungs to inflation thereby decreasing the tidal air flow. 7-(2β-[(3RS)-3-hydroxy-3-vinyl-trans-1-octenyl]-5-oxo-1α-cyclopentyl)-cis-5-heptenoic acid was then administered by aerosol, and the animals were then challenged again with acetylcholine, and the degree of inhibition of bronchoconstriction was thus determined. A minimum of two animals was used at each dose.

Results

| Total Aerosol Dose (mcg) | Mean % Protection VS ACH Bronchoconstriction |
|---|---|
| 1.5 × $10^{-4}$ | 30 |
| $10^{-3}$ | 72 |
| $10^{-2}$ | 60 |
| $10^{-1}$ | 74 |

B. Following the procedure described in Part A, above, but substituting 2β-[(3RS)-3-hydroxy-3-vinyl-trans-1-octenyl]-5-oxo-1α-cyclopentaneheptonic acid as the antagonist for acetyl choline, the inhibition of bronchoconstriction was determined.

Results[a]

| Total Aerosol Dose (mcg) | Mean % Protection VS ACH Bronchoconstriction |
|---|---|
| 1.5 × $10^{-4}$ | 43 |
| $10^{-3}$ | 78 |
| $10^{-2}$ | 70 |

[a]Minimum of 2 animals per dose

The subject matter which the applicants regard as their invention is particularly pointed out and distinctly claimed as follows:

1. A prostaglandin of the formula:

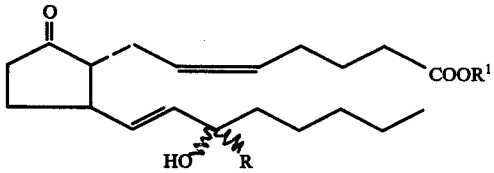

wherein R is benzyl; and $R^1$ is hydrogen, alkyl of from 1 to about 6 carbon atoms, alkali metal, or a pharmacologically acceptable cation derived from ammonia or a basic amine.

2. A compound as defined in claim 1 which is 7-(2β-[83RS)-3-benzyl-3-hydroxy-trans-1-octenyl]-5-oxo-1α-cyclopentyl)-cis-5-heptenoic acid.

* * * * *